(12) United States Patent
Nam et al.

(10) Patent No.: US 10,821,418 B2
(45) Date of Patent: Nov. 3, 2020

(54) SUPER ABSORBENT POLYMER

(71) Applicant: LG Chem, Ltd., Seoul (KR)

(72) Inventors: Dae Woo Nam, Daejeon (KR); Chang Sun Han, Daejeon (KR); Hyemin Lee, Daejeon (KR); Hwayoon Jung, Daejeon (KR); Hyung Ki Yoon, Daejeon (KR)

(73) Assignee: LG Chem, Ltd. (KR)

( * ) Notice: Subject to any disclaimer, the term of this patent is extended or adjusted under 35 U.S.C. 154(b) by 243 days.

(21) Appl. No.: 15/770,375

(22) PCT Filed: Jan. 10, 2017

(86) PCT No.: PCT/KR2017/000337
§ 371 (c)(1),
(2) Date: Apr. 23, 2018

(87) PCT Pub. No.: WO2017/142204
PCT Pub. Date: Aug. 24, 2017

(65) Prior Publication Data
US 2018/0304232 A1    Oct. 25, 2018

(30) Foreign Application Priority Data

Feb. 19, 2016 (KR) .................. 10-2016-0019951
Apr. 15, 2016 (KR) .................. 10-2016-0046495

(51) Int. Cl.
*B32B 5/16* (2006.01)
*B01J 20/26* (2006.01)
(Continued)

(52) U.S. Cl.
CPC ............. *B01J 20/267* (2013.01); *A61L 15/60* (2013.01); *B01J 20/103* (2013.01);
(Continued)

(58) Field of Classification Search
CPC ......... C08J 3/245; A61L 15/60; B01J 20/267; B01J 20/28004; C08F 292/00; C08K 3/36
(Continued)

(56) References Cited

U.S. PATENT DOCUMENTS 5,140,076 A    8/1992 Hatsuda et al.
5,409,771 A    4/1995 Dahmen et al.
(Continued)

FOREIGN PATENT DOCUMENTS

EP    2535027 A1    12/2012
JP    2001137704 A    5/2001
(Continued)

OTHER PUBLICATIONS

KR 2015-0020030, Translation copy. (Year: 2015).*
(Continued)

*Primary Examiner* — Hoa (Holly) Le
(74) *Attorney, Agent, or Firm* — Lerner, David, Littenberg, Krumholz & Mentlik, LLP

(57) ABSTRACT

The present invention relates to a super absorbent polymer exhibiting more improved liquid permeability and/or absorption rate while maintaining excellent absorption performance. Such super absorbent polymer comprises a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked through an alkylene carbonate having 2 to 5 carbon atoms, and satisfies predetermined physical properties.

10 Claims, 3 Drawing Sheets

(51) Int. Cl.

| | |
|---|---|
| *C08F 20/06* | (2006.01) |
| *C08K 3/36* | (2006.01) |
| *A61L 15/60* | (2006.01) |
| *C08F 4/40* | (2006.01) |
| *C08J 3/24* | (2006.01) |
| *C08J 3/075* | (2006.01) |
| *B01J 20/10* | (2006.01) |
| *B01J 20/28* | (2006.01) |
| *C08K 5/09* | (2006.01) |
| *C08K 5/00* | (2006.01) |

(52) U.S. Cl.
CPC ... *B01J 20/28004* (2013.01); *B01J 20/28016* (2013.01); *C08F 4/40* (2013.01); *C08F 20/06* (2013.01); *C08J 3/075* (2013.01); *C08J 3/24* (2013.01); *C08J 3/245* (2013.01); *C08K 3/36* (2013.01); *C08F 2810/20* (2013.01); *C08J 2333/02* (2013.01); *C08K 5/0025* (2013.01); *C08K 5/09* (2013.01)

(58) Field of Classification Search
USPC .................................................. 428/402–407
See application file for complete search history.

(56) References Cited

U.S. PATENT DOCUMENTS

| | | | |
|---|---|---|---|
| 5,562,646 A | 10/1996 | Goldman et al. | |
| 6,620,889 B1 | 9/2003 | Mertens et al. | |
| 7,572,864 B2 | 8/2009 | Mertens et al. | |
| 7,833,624 B2 | 11/2010 | Harren et al. | |
| 2002/0120074 A1 | 8/2002 | Wada et al. | |
| 2008/0075937 A1 | 3/2008 | Wada et al. | |
| 2008/0234645 A1 | 9/2008 | Dodge et al. | |
| 2009/0208748 A1 | 8/2009 | Torii et al. | |
| 2009/0227741 A1* | 9/2009 | Walden | C08F 222/1006 525/330.2 |
| 2010/0072421 A1* | 3/2010 | Kitano | A61L 15/24 252/194 |
| 2012/0329953 A1 | 12/2012 | Irie | |
| 2014/0193641 A1 | 7/2014 | Torii et al. | |
| 2015/0093575 A1 | 4/2015 | Naumann et al. | |
| 2015/0315321 A1 | 11/2015 | Won et al. | |
| 2015/0328358 A1 | 11/2015 | Kamphus et al. | |
| 2016/0199527 A1 | 7/2016 | Ota et al. | |
| 2016/0311985 A1 | 10/2016 | Jung et al. | |
| 2017/0015798 A1 | 1/2017 | Lee et al. | |
| 2017/0189575 A1 | 7/2017 | Lee et al. | |

FOREIGN PATENT DOCUMENTS

| | | | |
|---|---|---|---|
| JP | 2002239379 A | | 8/2002 |
| JP | 2004-2891 A | * | 8/2004 |
| JP | 2005067209 A | | 3/2005 |
| JP | 2009531158 A | | 9/2009 |
| JP | 2010522008 A | | 7/2010 |
| JP | 2014079324 A | | 5/2014 |
| JP | 2014515987 A | | 7/2014 |
| JP | 5658229 B2 | | 1/2015 |
| JP | 2015501684 A | | 1/2015 |
| JP | 2015503655 A | | 2/2015 |
| JP | 2015178099 A | | 10/2015 |
| KR | 19970010058 B1 | | 6/1997 |
| KR | 0143402 B1 | | 7/1998 |
| KR | 20000063574 A | | 11/2000 |
| KR | 100876827 B1 | | 1/2009 |
| KR | 20140038998 A | | 3/2014 |
| KR | 20140130034 A | | 11/2014 |
| KR | 20150020030 A | | 2/2015 |
| KR | 20150067729 A | | 6/2015 |
| KR | 20150142636 A | | 12/2015 |
| KR | 20150143167 A | | 12/2015 |
| WO | 2013078109 A1 | | 5/2013 |
| WO | 2015190879 A1 | | 12/2015 |

OTHER PUBLICATIONS

Search report from International Application No. PCT/KR2017/000337, dated May 1, 2017.
Schwalm, Reinhold, "UV Coatings: Basics, Recent Developments and New Applications." Elsevier Science, Dec. 21, 2006, p. 115.
Odian, George, "Principles of Polymerization." Second Edition, (Wiley, 1981), p. 203.
Extended European Search Report including Written Opinion for Application No. EP17753366.8 dated Nov. 12, 2018.
Third Party Observation for Application No. PCT/KR2017/000337 dated Jun. 19, 2018.

* cited by examiner

[FIG. 1]
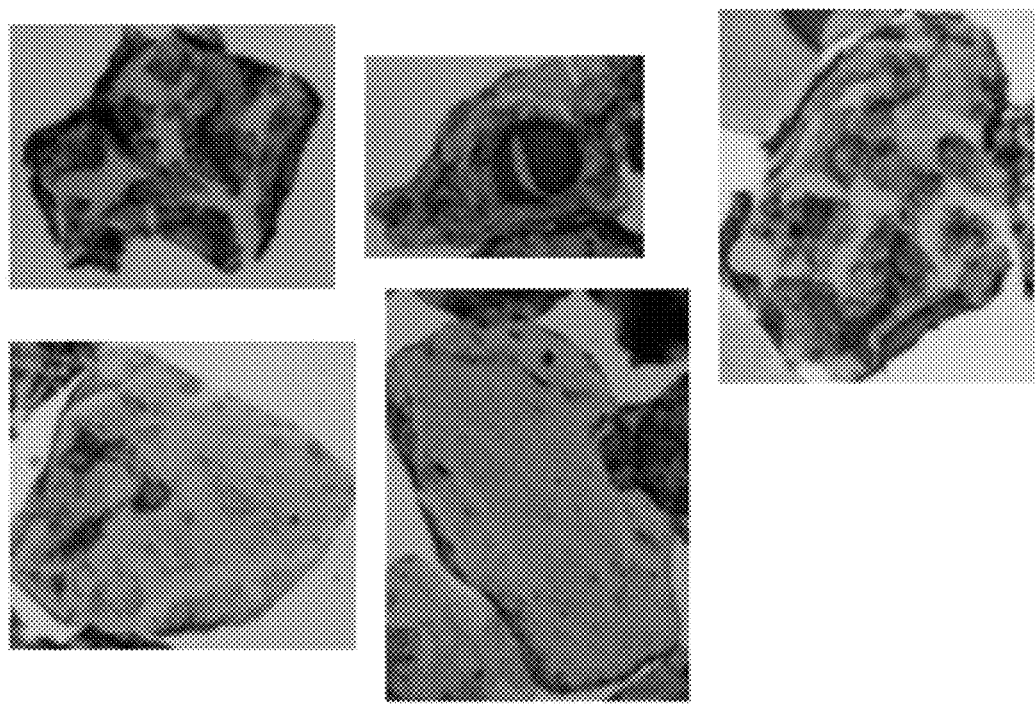

[FIG. 2]

[FIG. 3]
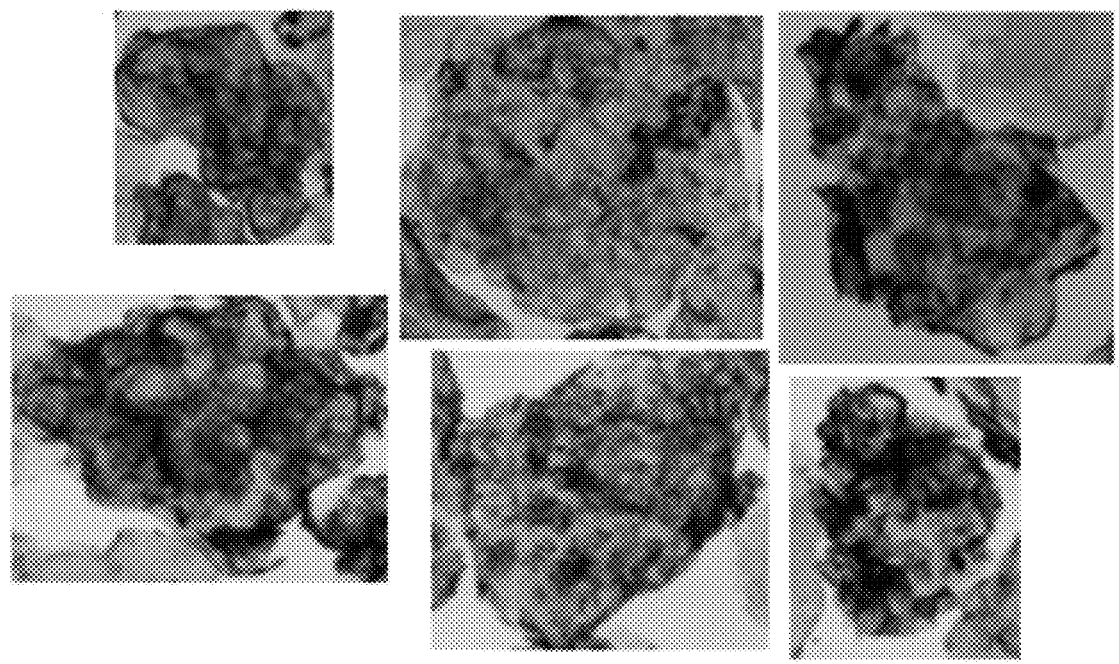

SUPER ABSORBENT POLYMER

CROSS-REFERENCE TO RELATED APPLICATION(S)

The present application is a national phase entry under 35 U.S.C. § 371 of International Application No. PCT/KR2017/000337, filed on Jan. 10, 2017, which claims the benefit of Korean Patent Application No. 10-2016-0019951, filed on Feb. 19, 2016, and Korean Patent Application No. 10-2016-0046495, filed on Apr. 15, 2016, the disclosures of which are incorporated herein by reference.

TECHNICAL FIELD

The present invention relates to a super absorbent polymer exhibiting more improved liquid permeability and/or absorption rate while maintaining excellent absorption performance.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

In particular, in recent years, as studies have been conducted to provide diapers exhibiting excellent performance while having a thinner thickness and a light weight, much attention has been focused on providing a super absorbent polymer having more improved liquid permeability and an absorption rate. In order to achieve such a fast absorption rate and improved liquid permeability, it is necessary that the surface strength of the super absorbent polymer particles, particularly the surface cross-linked layer, is made harder and the gel strength is higher. Consequently, it becomes necessary for urine to be evenly and rapidly dispersed in the absorber core of the diaper.

However, in the case where it is tried to increase the gel strength and increase the liquid permeability and absorption rate through a method previously known in the art, there were a drawback that the basic absorption performance (absorbency under no pressure and under pressure) itself is greatly lowered.

Therefore, there is a continuing need to develop a technique capable of providing a super absorbent polymer having more improved liquid permeability and absorption rate while maintaining excellent basic absorption performance.

Technical Problem

It is one object of the present invention to provide a super absorbent polymer exhibiting more improved liquid permeability and/or absorption rate while maintaining excellent absorption performance.

Technical Solution

The present invention provides a super absorbent polymer comprising:

a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked via an alkylene carbonate having 2 to 5 carbon atoms, wherein the super absorbent polymer has the following features:

a centrifuge retention capacity (CRC) for a physiological saline solution (0.9 wt % sodium chloride aqueous solution) for 30 minutes is 25 to 35 g/g, an absorbency under pressure (AUP) under 0.7 psi for a physiological saline solution (0.9 wt % sodium chloride aqueous solution) for 1 hour is 23.5 to 30 g/g, a saline flow conductivity (SFC) for a physiological saline solution (0.685 wt % sodium chloride aqueous solution) ($\cdot 10^{-7}$ cm$^3 \cdot$s/g) is 60 to 130 ($\cdot 10^{-7}$ cm$^3 \cdot$s/g), and a particle strength is 1.5 kgf or more, or 1.5 kgf to 2.5 kgf.

The above super absorbent polymer may more suitably exhibit a characteristic that T-20 indicating the time required for absorbing 1 g of the super absorbent polymer to 20 g of an aqueous solution of sodium chloride and alcohol ethoxylate having 12 to 14 carbon atoms, is 100 to 190 seconds.

Hereinafter, the super absorbent polymer according to specific embodiments of the invention will be described in more detail. However, this is merely presented as an example of the present invention, and will be apparent to those skilled in the art that the scope of the present invention is not limited to these embodiments, and various modifications can be made to the embodiments within the scope of the present invention.

In addition, unless stated otherwise throughout this specification, the term "comprises" or "contains" means to include any constituent element (or constituent component) without particular limitation, and it cannot be interpreted as a meaning of excluding an addition of other constituent element (or constituent component).

According to one embodiment of the present invention, there is provided a super absorbent polymer comprising:

a base polymer powder including a first cross-linked polymer of a water-soluble ethylenically unsaturated monomer having at least partially neutralized acidic groups; and a surface cross-linked layer formed on the base polymer powder and including a second cross-linked polymer in which the first cross-linked polymer is further cross-linked via an alkylene carbonate having 2 to 5 carbon atoms, wherein the super absorbent polymer has the following features:

a centrifuge retention capacity (CRC) for a physiological saline solution (0.9 wt % sodium chloride aqueous solution) for 30 minutes is 25 to 35 g/g, an absorbency under pressure (AUP) under 0.7 psi for a physiological saline solution (0.9 wt % sodium chloride aqueous solution) for 1 hour is 23.5 to 30 g/g, a saline flow conductivity (SFC) for a physiological saline solution (0.685 wt % sodium chloride aqueous solution) ($\cdot 10^{-7}$ cm$^3 \cdot$s/g) is 60 to 130 ($\cdot 10^{-7}$ cm$^3 \cdot$s/g), and a particle strength is 1.5 kgf or more, or 1.5 kgf to 2.5 kgf.

The super absorbent polymer of one embodiment may further exhibit a characteristic that T-20 indicating the time required for absorbing 1 g of the super absorbent polymer to 20 g of an aqueous solution of sodium chloride and alcohol ethoxylate having 12 to 14 carbon atoms, is 100 to 190 seconds.

The present inventors have conducted continuous research to further improve a liquid permeability and/or absorption rate of the super absorbent polymer. As a result, the inventors have found that, as the base polymer powder exhibiting a high FSR of, for example, 0.22 g/g·s or more is obtained by optimizing the conditions of the production process of the super absorbent polymer, for example, the pulverization and classification conditions to be described later, and the surface crosslinking proceeds under specific surface crosslinking conditions (for example, specific silica particles are used together during surface crosslinking, etc.), it is possible to provide a super absorbent polymer which maintains excellent absorption performance while exhibiting greatly improved liquid permeability and/or absorption rate compared to those previously known.

Particularly, it was found that, as a surface crosslinking liquid containing a specific silica particle and a specific surface crosslinking agent are added and then the surface crosslinking proceeds under specific temperature-raising conditions, the surface cross-linked layer having a certain level or more of thickness can be evenly formed on the base polymer powder having FSR, and further, the overall surface crosslinking ratio can be greatly increased.

This is probably because, as the surface crosslinking liquid and the base polymer powder are mixed in a state in which the silica particles are well dispersed in the surface crosslinking liquid, the surface crosslinking agent is uniformly coated onto the base polymer powder, and as a result, a uniform surface cross can be formed. That is, this is because, not only the silica particles can assist in proper formation of the surface cross-linked layer but also it can be included in the cross-linked structure of the second cross-linked polymer, thereby further tightening the cross-linked structure. Further, it is predicted that the surface crosslinking reaction appropriately occurs around each silica particle during surface crosslinking, and the second cross-linked polymer can be effectively formed.

Thus, the super absorbent polymer particles can exhibit improved liquid permeability defined as SFC of 60 to 130($\cdot 10^{-7}$ cm$^3 \cdot$s/g) together with high strength (for example, particle strength and gel strength), particularly high particle strength of 1.5 kgf or more. Also, the super absorbent polymer of one embodiment can exhibit excellent absorption performance defined by the CRC of 25 to 35 g/g and the AUP of 23.5 to 30 g/g, as the internal crosslinking structure and the surface crosslinking structure are optimized, and further may exhibit an excellent absorption rate defined as T-20 of 100 to 190 seconds.

Thus, the super absorbent polymer of one embodiment exhibits improved liquid permeability/or absorption rate and superior absorption performance than those previously known, and thus can be very preferably applied to various sanitary materials such as diapers with a content of pulp decreased.

Meanwhile, the super absorbent polymer can be used together with specific silica particles (for example, fumed silica particles, more suitably fumed silica particles and colloidal silica particles) during surface crosslinking, These silica particles are contained in the surface crosslinking liquid, so that the surface crosslinking solution exhibits a contact angle of 60° or less, or 5 to 60° on a PET substrate (Mitsuibishi Polyester Film, Grade: O0300E). Thus, the super absorbent polymer of one embodiment may further include fumed silica particles, more suitably fumed silica particles and colloidal silica particles, contained in the surface cross-linked layer (for example, in the cross-linked structure thereof).

As these silica particles are contained in the cross-linked structure on the surface cross-linked layer and particularly are uniformly contained on the surface cross-linked layer, the super absorbent polymer of one embodiment can adequately exhibit improved liquid permeability and/or absorption rate, and the enhanced physical properties can be continuously expressed and maintained despite the passage of time.

As the fumed silica particles, any of commercially available silica particles satisfying the above-mentioned requirements, for example, silica particles represented by the product names such as Aerosil, Tixosil or DM30S, can be used without particular limitation. Similarly, any of commercially available water-dispersible silica particles satisfying the above-mentioned requirements, for example, water-dispersible silica particles represented by the product names such as ST-30, ST-O, ST-N, ST-C or ST-AK can be suitably used as the colloidal silica particles, thereby making the physical properties of the super absorbent polymer of one embodiment more excellent.

On the other hand, the super absorbent polymer may have a centrifuge retention capacity (CRC) of 25 to 35 g/g, or 26 to 32 g/g.

In this case, the centrifuge retention capacity (CRC) for the physiological saline solution can be calculated by the following Calculation Equation 1 after absorbing the super absorbent polymer in a physiological saline solution over a period of 30 minutes.

$$CRC(g/g) = \{[W_2(g) - W_1(g) - W_0(g)]/W_0(g)\} \quad \text{[Calculation Equation 1]}$$

in Calculation Equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is the weight of the device including the super absorbent polymer, measured after soaking the super absorbent polymer in a physiological saline solution at room temperature for 30 minutes, and then dehydrating the same by using a centrifuge at 250 G for 3 minutes.

Meanwhile, the super absorbent polymer may have an absorbency under pressure (AUP) of 23.5 to 30 g/g, or 24 to 28 g/g.

The absorbency under pressure (AUP) can be calculated by the following Calculation Equation 2 after absorbing the super absorbent polymer in a physiological saline solution under pressure of 0.7 psi over a period of 1 hour.

$$AUP(g/g) = [W_4(g) - W_3(g)]/W_0(g) \quad \text{[Calculation Equation 2]}$$

in Calculation Equation 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

As the super absorbent polymer of one embodiment exhibits the centrifuge retention capacity (CRC) and the absorbency under pressure (AUP) within the above-described range, the super absorbent polymer can basically exhibit excellent absorption performance under no pressure and under pressure and thus can be suitably used for various sanitary materials such as diapers.

Meanwhile, the super absorbent polymer of one embodiment can exhibit the above-described absorption performance and the characteristic that the particle strength is 1.5 kgf or more, or 1.5 kgf to 2.5 kgf, or 1.6 kgf to 2.3 kgf. Such a particle strength can be measured and defined as the maximum force which is applied until a single super absorbent polymer particle having a particle size of 600 to 850 μm is pressed and crushed.

As the super absorbent polymer of one embodiment exhibits high particle strength, the super absorbent polymer can exhibit absorption properties such as higher liquid permeability and absorbency under pressure. This is because, when the super absorbent polymer is contained in a sanitary material such as a diaper, it can exhibit excellent shape retaining property and strength despite the force applied thereto, and thus maintain excellent liquid permeability and absorption capacity.

Further, the super absorbent polymer of one embodiment can exhibit the characteristic that the horizontal gel strength G' measured after absorbing and swelling a physiological saline solution (0.9 wt % sodium chloride aqueous solution) for 1 hour is 10,000 to 15,000 Pa, or 11,000 to 15,000 Pa.

The horizontal gel strength G' can better reflect excellent liquid permeability under the environments of actually using the super absorbent polymer. That is, conventionally the liquid permeability of the super absorbent polymer can be determined to be highly relevant depending on whether to exhibit excellent shape retaining property and high gel strength, irrespective of the force applied in the horizontal direction when the super absorbent polymer was contained in the sanitary materials such as diapers. The horizontal gel strength can better reflect the gel strength directly related to such liquid permeability. Therefore, it has been found that the super absorbent polymer of one embodiment in which the horizontal gel strength G' satisfies the above-mentioned range exhibits excellent liquid permeability, and thus can be used very preferably for sanitary materials such as diapers.

This horizontal gel strength G' can be measured by a method comprising the following respective steps by using a commercialized rheometer, after a physiological saline has been absorbed to the super absorbent polymer for 1 hour.

1) a step of absorbing a physiological saline solution to the super absorbent polymer to swell the super absorbent polymer;

2) a step of positioning the swelled super absorbent polymer between plates of a rheometer having a predetermined interval to pressurize the two plate surfaces;

3) a step of confirming a shear strain in the linear viscoelastic regime section where storage modulus and loss modulus are steady, while increasing the shear strain using the rheometer under vibration; and 4) a step of measuring the storage modulus and the loss modulus of the swelled super absorbent polymer under the confirmed shear strain, respectively, and measuring the average value of the storage modulus as a gel strength.

Further, the super absorbent polymer of one embodiment may have a saline flow conductivity for a physiological saline solution (SFC) of 60 to $130 \cdot 10^{-7}$ cm$^3 \cdot$s/g, or 70 to $130 \cdot 10^{-7}$ cm$^3 \cdot$s/g. This saline flow conductivity for a physiological saline solution (SFC) can be measured and calculated according to the method already well-known to those skilled in the art, for example, the method disclosed in Columns 54 to 59 of U.S. Pat. No. 5,562,646.

As the super absorbent polymer of one embodiment exhibits such SFC range, it can exhibit improved liquid permeability than previously known.

In addition, the super absorbent polymer of one embodiment has T-20 of 100 to 190 seconds, or 130 to 190 seconds, which indicates the time required for absorbing 1 g of the super absorbent polymer to 20 g of an aqueous solution of sodium chloride and alcohol ethoxylate having 12 to 14 carbon atoms, and it can exhibit a high absorption rate defined thereby. Such T-20 can be calculated and measured as follows. For example, an aqueous solution in which 9 g of sodium chloride and 1 g of Lorodac (main component: alcohol ethoxylate having 12 to 14 linear carbon atoms, CAS #68439-50-9) are dissolved in 1 L of distilled water, and the T-20 is calculated and measured with the time required for absorbing 1 g of the super absorbent polymer to 20 g of this aqueous solution. Specific measurement method of T-20 is described in detail on pages 13 to 18 of European Patent Publication No. 2535027.

In the preparation method described later, the super absorbent polymer is produced so as to have a larger surface area through a certain pulverizing and classification process, and therefore, it can be seen to exhibit a high absorption rate together with the above excellent liquid permeability and absorption performance.

Further, the super absorbent polymer of one embodiment described above may have a crosslinking ratio of 30% to 90%, or 33% to 60%, measured after swelling the super absorbent polymer in a physiological saline solution (0.9 wt % sodium chloride aqueous solution) to which 20 ppmw of Toluidine Blue O (TBO, CAS #92-31-9) has been added for 16 hours.

The surface crosslinking ratio is an index first introduced by the present inventors in order to objectively evaluate the degree of surface crosslinking. After 0.5 g of a super absorbent polymer (powder having a particle size of 300 to 600 μm is classified and taken) is swollen in 50 mL of physiological saline solution dissolved by adding the TBO for 16 hours, the resultant can be observed with a Stereotype Microscope and evaluated as follows.

First, the photographs (image resolution: 1024×768, transmission mode, stereotype) of the whole particles of the super absorbent polymer after swelling at 10 magnification are photographed, and the size and length of the photographs were adjusted so that the total number of particles in the photographs is 200 to 300. Next, the paper size is set to A4 size with Microsoft's Power Point 2010 version, the photographed picture is pasted, and the picture size is adjusted to 19 cm×25.33 cm. Then, the contrast of the photograph is adjusted to about 40% in black and white, and the brightness of the photograph is adjusted at an appropriate brightness, for example, at a reflectance of about 18%.

As a result, for example, photographs as shown in FIGS. 1 to 3 can be obtained. In this case, as shown in FIG. 1, particles having stripes with a width of 2 mm or more and a length of 5 mm or more formed on the particles can be evaluated as surface cross-linked particles, and as shown in FIGS. 2 and 3, particles without stripe formation can be evaluated as surface non-cross-linked particles. Under this criterion, the proportion of the number of the surface cross-linked particles among the particles of the entire super absorbent polymer produced under the same conditions can be defined as the surface crosslinking ratio. For reference, the stripes having a width of 2 mm or more and a length of 5 mm or more are observed while the SHELL of the super absorbent polymer of the surface cross-linked layer breaks. The degree of surface crosslinking can be confirmed and evaluated by the traces that the SHELL has been broken by swelling. The surface crosslinking ratio can be calculated according to the following formula: Surface crosslinking ratio (%)=["Number of particles evaluated as surface cross-linked particles"/"Number of total particles in photograph"]×100.

As supported by the following examples, it has been found that as the super absorbent polymer of one embodiment satisfies a high surface crosslinking ratio as compared with the super absorbent polymer prepared by a previous method. This is presumably because, as specific silica particles are used during surface crosslinking and they are contained in the surface crosslinked layer, a uniform surface cross-linked layer can be better formed on each super absorbent polymer particle.

As the super absorbent polymer of one embodiment exhibits such a high surface crosslinking ratio, it can exhibit high particle strength, gel strength, improved liquid permeability and the like, and it can have excellent absorption rate and absorption performance (for example, absorbency under pressure).

Meanwhile, the super absorbent polymer of one embodiment can be typically obtained by polymerizing a water-soluble ethylenically unsaturated monomer having at least partially neutralized acidic groups, such as a mixture of acrylic acid and its sodium salt in which at least a part of carboxylic acid is neutralized with sodium salt or the like, in the presence of an internal crosslinking agent. More specifically, the super absorbent polymer can be obtained by carrying out a crosslinking polymerization of the above-mentioned monomer in the presence of an internal crosslinking agent to obtain a base polymer powder, drying, pulverizing and classifying the base polymer powder under certain conditions, and then surface-crosslinking the base polymer powder in the presence of a predetermined surface crosslinking agent and a specific silica particle to prepare a cross-linked polymer.

More specifically, it has been found that, as the base polymer powder having high gel strength is obtained by adjusting the type and content of an internal crosslinking agent, the polymerization conditions, and the like, the FSR of the base polymer powder is controlled through pulverization and classification conditions, and then, for example, the surface crosslinking proceeds under specific conditions using specific silica particles, thereby preparing a super absorbent polymer of one embodiment exhibiting the above-mentioned various physical properties.

A method for preparing the super absorbent polymer according to one embodiment may comprise the steps of:

carrying out a crosslinking polymerization of a water-soluble ethylenically unsaturated monomer having at least partially neutralized acidic groups in the presence of an internal crosslinking agent to form a hydrogel polymer including a first cross-linked polymer;

drying, pulverizing, and classifying the hydrogel polymer to form a base polymer powder; and heat-treating the base polymer powder in the presence of a surface crosslinking liquid containing fumed silica particles, more suitably fumed silica particles and colloidal silica particles, and a surface cross-linking agent of alkylene carbonate having 2 to 5 carbon atoms to perform a surface crosslinking.

As the silica particles are contained in the surface crosslinking liquid, the surface crosslinking solution can exhibit a contact angle of 60° or less, or 5 to 60° on a PET substrate (Mitsuibishi Polyester Film, Grade: O0300E).

According to this preparation method, the surface crosslinking proceeds by using a surface crosslinking liquid containing the above-mentioned specific silica particles and an alkylene carbonate-based surface crosslinking agent during surface crosslinking. This makes it possible to uniformly form a surface cross-linked layer having a certain level or more of thickness, and to prepare a super absorbent polymer of one embodiment exhibiting excellent absorption performance together with a high surface crosslinking ratio, more improved particle strength, gel strength and liquid permeability.

In such super absorbent polymer, the water-soluble ethylenically unsaturated monomer may include at least one selected from the group consisting of anionic monomers of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloyl-propanesulfonic acid or 2-(meth)acrylamido-2-methylpropanesulfonic acid, and their salts; non-ionic, hydrophilic group-containing monomers of (meth)acrylamide, N-substituted (meth)acrylate, 2-hydroxyethyl(meth)acrylate, 2-hydroxypropyl(meth)acrylate, methoxypolyethylene glycol (meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternary product. Among them, acrylic acid and/or a salt thereof, for example, an alkali metal salt such as acrylic acid and/or a sodium salt thereof having at least partially neutralized acrylic acids can be used, and the use of these monomers enables production of a super absorbent polymer having more excellent physical properties. In the case of using acrylic acid and its alkali metal salt as a monomer, it is possible to use acrylic acid after neutralizing at least a part thereof with a basic compound such as caustic soda (NaOH).

Further, as the internal crosslinking agent for crosslinking the monomer, at least one selected form the group consisting of bis(meth)acrylamide having 8 to 12 carbon atoms, poly (meth)acrylate of polyol having 2 to 10 carbon atoms and poly(meth)acrylate of polyol having 2 to 10 carbon atoms can be used. More specifically, as the internal crosslinking agent, one or more poly(meth)acrylates of polyols selected from the group consisting of polyethylene glycol di(meth) acrylate, polypropyleneoxy di(meth)acrylate, glycerin diacrylate, glycerin triacrylate and trimethylol triacrylate can be suitably used. Among them, as an internal crosslinking agent such as polyethylene glycol di(meth)acrylate is used, the internal crosslinking structure is optimized and a base polymer powder or the like having high gel strength can be obtained, Thereby, the super absorbent polymer satisfying excellent physical properties can be more appropriately obtained.

The specific certain internal crosslinking agent can be used in a ratio of 0.3 or more parts by weight, or 0.3 to 1.0 part by weight relative to 100 parts by weight of acrylic acid, based on 100 parts by weight of non-neutralized acrylic acid contained in the monomer. The base polymer powder having a high gel strength before surface crosslinking can be suitably obtained according to the range of the content of the internal crosslinking agent, and a super absorbent polymer satisfying the physical properties of one embodiment can be more effectively obtained.

After carrying out a crosslinking polymerization of the monomer using the internal crosslinking agent, processes such as drying, pulverizing and classifying are performed to obtain a base polymer powder. Through the processes such as the pulverizing and classifying, the base polymer powder and the super absorbent polymer obtained therefrom are suitably prepared and provided so as to have a particle size of 150 to 850 μm. More preferably, at least about 95% by weight of the base polymer powder and the super absorbent polymer obtained therefrom have a particle size of 150 to 850 μm, and fine powders having a particle size of less than 150 μm can be less than 3% by weight, or less than 1.5% by weight. Particularly, it is possible to obtain a base resin powder satisfying a high FSR by controlling such pulverization and classification conditions, and thereby, a super absorbent polymer of one embodiment can be suitably obtained. The conditions of the pulverization and classification will be described later.

In addition, the super absorbent polymer of one embodiment may comprise a base polymer powder including a first cross-linked polymer prepared by the above-mentioned method, and a surface cross-linked layer including a second cross-linked polymer in which the first cross-linked polymer is further cross-linked by surface crosslinking. The surface crosslinking for forming the surface cross-linked layer may be performed by heat-treating the base polymer powder in the presence of the surface crosslinking liquid containing the above-mentioned specific silica particles and the surface crosslinking agent of an alkylene carbonate having 2 to 5 carbon atoms. The silica particles usable in this case have been described above, and thus more specific description thereon will be omitted.

Further, more suitable examples of the alkylene carbonate having 2 to 5 carbon atoms which can be used as the surface crosslinking agent include ethylene carbonate, propylene carbonate, glycerin carbonate, butylene carbonate or the like, and two or more selected among them may be used together.

On the other hand, hereinafter, the method capable of preparing the super absorbent polymer of one embodiment described above will be described in more detail according to respective steps. However, with regard to the monomers, internal crosslinking agent, surface crosslinking agent, silica particles and particle size distribution already described above, duplicating explanation thereon will be omitted, and the remaining process configuration and condition will be described in detail for each step of the process.

The method for preparing the super absorbent polymer may comprise the steps of: forming a hydrogel polymer including a first cross-linked polymer by carrying out a thermal polymerization or photo polymerization of a monomer composition including a water-soluble ethylenically unsaturated monomer, an internal crosslinking agent and a polymerization initiator; drying the hydrogel polymer; pulverizing and classifying the dried polymer to form a base polymer powder; and carrying out a surface crosslinking of the base polymer powder using a surface crosslinking liquid including the above-mentioned silica particles and a surface crosslinking agent.

In the above preparation method, the monomer composition includes a water-soluble ethylenically unsaturated monomer, an internal crosslinking agent and a polymerization initiator, and the types of the monomers are the same as those already described above.

Further, in the above composition, the concentration of the water-soluble ethylenically unsaturated monomer may be 20 to 60% by weight, or 40 to 50% by weight based on the entire monomer composition including the respective raw materials and solvents described above, and it may be controlled to be an adequate concentration in consideration of the polymerization time, the reaction conditions or the like. However, when the concentration of the monomer is too low, the yield of the super absorbent polymer is low and there may be a problem with economics. By contrast, when the concentration is too high, there may be problems on the process that some of the monomers may be deposited or the pulverizing efficiency of the prepared hydrogel polymer appears to be low in the pulverizing process, and thus the physical properties of the super absorbent polymer may decrease.

Further, the polymerization initiator is not particularly limited as long as it is an initiator that is generally used in the preparation of the super absorbent polymer.

Specifically, the polymerization initiator may include a thermal polymerization initiator or a photo polymerization initiator by UV irradiation, according to the polymerization method. However, even in the case of photo polymerization method, a thermal polymerization initiator may be additionally included because a certain amount of heat is generated by the irradiation of UV ray and the like, and a certain amount of heat is generated in accordance with the progress of the polymerization reaction, which is an exothermic reaction, and thus, a thermal polymerization initiator may be further included.

The photo polymerization initiator that can be used is not particularly limited by its constitution as long as it is a compound capable of forming a radical by light such as ultraviolet rays.

The photo-polymerization initiator used herein may include, for example, at least one selected from the group consisting of benzoin ether, dialkyl acetophenone, hydroxyl alkylketone, phenyl glyoxylate, benzyl dimethyl ketal, acyl phosphine and α-aminoketone. Meanwhile, specific examples of the acyl phosphine, commercialized lucirin TPO, namely, 2,4,6-trimethyl-benzoyl-trimethyl phosphine oxide may be used. More various photo polymerization initiators are well disclosed in "UV Coatings: Basics, Recent Developments and New Application" written by Reinhold Schwalm, (Elsevier, 2007), p 115, however the example of the photo polymerization initiator is not limited thereto.

The photo polymerization initiator may be included in a concentration of 0.005% to 1.0 by weight based on the monomer composition. When the concentration of the photo polymerization initiator is too low, the polymerization rate may become slow, and when the concentration of the photo polymerization initiator is too high, the molecular weight of the super absorbent polymer becomes small and the physical properties may become uneven.

And, as the thermal polymerization initiator, one or more selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like; and examples of the azo-based initiator include 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) or the like. More various thermal polymerization initiators are well disclosed in "Principle of Polymerization" written by Odian, (Wiley, 1981), p 203, however the example of the thermal polymerization initiator is not limited thereto.

The thermal polymerization initiator may be included in a concentration of 0.001 to 0.5% by weight with respect to the monomer composition. If the concentration of such a thermal polymerization initiator is too low, additional thermal polymerization hardly occurs and the effect due to the addition of the thermal polymerization initiator may be insignificant. If the concentration of the thermal polymerization initiator is excessively high, the molecular weight of the super absorbent polymer may be small and the physical properties may become uneven.

In addition, the types of the internal crosslinking agent contained together with the monomer composition are the same as those already described above. The above internal crosslinking agent may be used in a ratio of 0.01 to 2.0 parts by weight based on the monomer composition so that the polymerized polymer can be cross-linked. The above internal crosslinking agent may be used in a ratio of 0.3 or more parts by weight, or 0.3 to 1.0 part by weight relative to 100 parts by weight of the non-neutralized acrylic acid contained in the monomer. As the internal crosslinking agent is used within such content range, a gel strength range before the surface crosslinking can be suitably satisfied. By using the above, the super absorbent polymer more suitably satisfying the physical properties according to one embodiment can be obtained.

In addition, the monomer composition may further include additives such as a thickener, a plasticizer, a preservation stabilizer, an antioxidant, and so on, as needed.

The monomer composition may be prepared in the form of solution wherein the raw materials such as the water-soluble ethylenically unsaturated monomer, the photo polymerization initiator, the thermal polymerization initiator, the internal crosslinking agent, and the additives are dissolved in a solvent.

At this time, the above-described solvents can be used without limitation in the constitution as long as they are those which can dissolve said components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination.

The solvent may be included in the residual quantity excluding the components disclosed above based on the total content of the monomer composition.

Meanwhile, the method of forming a hydrogel polymer by subjecting such monomer composition to the thermal polymerization or photo polymerization can be used without limitation in the constitution as long as it is a method generally used in the polymerization.

Specifically, the polymerization method is largely classified into the thermal polymerization and the photo polymerization according to the polymerization energy source. Usually, the thermal polymerization may be carried out in the reactor like kneader equipped with agitating spindles, and the photo polymerization may be carried out in the reactor equipped with movable conveyor belt, however the polymerization method disclosed above is only one example, and the present invention is not limited to the polymerization methods disclosed above.

As an example, the hydrogel polymer obtained by subjecting to the thermal polymerization in the reactor like kneader equipped with the agitating spindles disclosed above by providing hot air thereto or heating the reactor may have the size of centimeters or millimeters when it is discharged from the outlet of the reactor, according to the types of the agitating spindles equipped in the reactor. Specifically, the size of the obtained hydrogel polymer can be variously shown according to the concentration of the monomer composition fed thereto, the feeding speed, and the like, and the hydrogel polymer of which the weight average particle size is 2 to 50 mm can be generally obtained.

Further, as described above, when the photo polymerization is carried out in a reactor equipped with a movable conveyor belt, the hydrogel polymer typically obtained may be a hydrogel polymer in a sheet-type having a width of the belt. In this case, the thickness of the polymer sheet may vary according to the concentration of the monomer composition fed thereto and the feeding speed, and the polymer sheet is preferably controlled to have a thickness of 0.5 to 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the thickness of the polymer due to the excessively high thickness.

In this case, the hydrogel polymer thus obtained by the above-described method may have typically a water content of 40 to 80% by weight. Meanwhile, the term "water content" as used herein means a weight occupied by moisture with respect to a total amount of the hydrogel polymer, which may be the value obtained by subtracting the weight of the dried polymer from the weight of the hydrogel polymer. Specifically, the water content is defined as a value calculated by measuring the weight loss according to evaporation of water in the polymer during the drying process of increasing the temperature of the polymer with infrared heating. At this time, the water content is measured under the drying conditions which are determined as follows; the temperature is increased from room temperature to 180° C., then the temperature is maintained at 180° C., and the total drying time is set to 20 minutes, including 5 minutes for the temperature rising step.

Next, the step of drying the hydrogel polymer thus obtained is performed.

If necessary, a gel-pulverizing step may be performed before the drying step, in order to increase the efficiency of the drying step.

In this case, a pulverizing device used herein may include, but the constitution is not limited to, any one selected from the group consisting of a vertical pulverizing device, a turbo cutter, a turbo grinder, a rotary cutter mill, a cutter mill, a disc mill, a shred crusher, a crusher, a chopper, and a disc cutter, but is not limited thereto.

In this case, the gel-pulverizing step may be performed so that the hydrogel polymer has a particle size of 0.5 to 10 mm. In a more specific example, the gel-pulverizing step is carried out by a process in which a pulverizing device such as Meat Chopper (SL Company, SM3-2) or a chopper similar thereto is used, and an inverter for axis control (for example, manufacturer: LS Industrial Systems, model name: iG5A) is installed, an S-13 mm perforated plate (for example, an aperture ratio of 20 to 40%, more specifically, 25% or 34%) is installed on a discharge port of the pulverizing device, and the hydrogel polymer is passed through a pulverizing device while rotating the shaft at a speed of about 10 to 100 Hz (for example, 60 Hz). Thereby, a base polymer powder having an FSR of 0.22 g/g·s or more can be more effectively obtained, and thus a super absorbent polymer of one embodiment can be produced.

The hydrogel polymer gel-pulverized as above or immediately after polymerization without the gel-pulverizing step is subjected to a drying step. At this time, the drying temperature of the drying step may be 150 to 250° C. When the drying temperature is less than 150° C., there is a concern that the drying time becomes excessively long or the physical properties of the super absorbent polymer finally formed may be deteriorated, and when the drying temperature is higher than 250° C., only the surface of the polymer is excessively dried, and thus there is a concern that fine powder may be generated during the subsequent pulverization process and the physical properties of the super absorbent polymer finally formed may be deteriorated. Therefore, the drying process may be preferably performed at a temperature of 150 to 200° C., and more preferably 160 to 190° C.

Meanwhile, the drying step may be carried out for 20 to 90 minutes, in consideration of the process efficiency, but is not limited thereto.

The drying method of the drying step may be selected and used in the drying step without limitation in the constitution if it can be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be about 0.1 to about 10% by weight. This water content can be measured at a temperature of about 180° C. for 40 minutes.

Next, the dried polymer obtained from the drying step is subjected to a (finely) pulverizing step.

The polymer powder obtained from the pulverization step may have a particle size of 150 to 850 µm. Specific examples of a milling device that can be used for pulverizing to have the above particle size may include a pin mill, a hammer mill, a screw mill, a roll mill, a disc mill, a jog mill, other mixer type mill, or the like, but the present invention is not limited thereto.

In a specific example of the (finely) pulverizing step, it can be carried out using a food mixer type pulverizing device (manufacturer: HANIL, model name: HMF-3000S), the dried polymer powder is placed in the pulverizing device, and pulverization can be carried out for an appropriate time (for example, 15 seconds based on 500 g) according to the amount.

Consequently, the base polymer powder having an FSR of 0.22 g/g·s or more can be more effectively obtained, and thereby, the super absorbent polymer of one embodiment can be more effectively obtained.

In order to properly control the physical properties of the super absorbent polymer powder finally produced after the pulverization step, a separate classifying step can be performed according to the particle sizes of the polymer powders obtained from the pulverization. In this classifying step, for example, the pulverized polymer powder is put in a classifier (for example, Restsch, AS200, etc.) and classified with an amplitude of 1.5 mm into five mesh sizes (for example, combination of classified meshes: #25/#30/#50/#100/PAN) and respective classified particles can be collected. Thereafter, if necessary, the large particles collected on the #25 sieve may be further pulverized for an appropriate time, which may be repeated plural times.

Through the above-described pulverizing and classifying steps, a polymer having a particle size of 150 to 850 µm is classified and only particle having such particle size is subjected to the surface crosslinking reaction and finally can be commercialized. The particle size distribution of the base polymer powder obtained through such process has been described above, and thus more specific description thereon will be omitted.

The above-mentioned base polymer powder may exhibit a FSR (Free Swell Ratio) of 0.22 g/g·s or more, or 0.22 g/g·s to 0.35 g/g·s before surface cross-linking, and thereby a super absorbent polymer having an excellent absorption rate and the like can be appropriately produced. The FSR of the base polymer powder was classified into #30 to #50 among the above mesh sizes (for example, those having a particle size of 300 to 600 µm), and the FSR of the base polymer powder was measured and calculated according to the method described on pages 22 to 23 of European Patent Publication No. 2535027.

On the other hand, after obtaining the base polymer powder through the pulverizing and/or classifying steps, the super absorbent polymer of one embodiment can be prepared through the surface crosslinking step. The types of the surface crosslinking agent, the hydrophobic and/or hydrophilic inorganic particles usable in the surface crosslinking step have been described above, and thus more specific description thereon will be omitted.

In this surface crosslinking step, the base polymer powder is subjected to a surface crosslinking with a surface crosslinking liquid containing the above-mentioned silica particles, that is, fumed silica particles and/or colloidal silica particles and a surface crosslinking agent.

The surface cross-linking liquid may include 0.01 to 0.1 parts by weight of the fumed silica particles, 0.005 to 0.2 parts by weight of the colloidal silica particles and 0.1 to 3 parts by weight of the surface cross-linking agent based on 100 parts by weight of the base resin powder. In addition, the surface cross-linking solution may further include a polycarboxylic acid-based copolymer disclosed in Korean Patent Laid-Open Publication No. 2015-0143167 (Korean Patent Application No. 2014-0072343). Such copolymer can be contained in the surface crosslinking liquid in a content of 0.01 to 0.1 based on 100 parts by weight of the base polymer powder. The use of these specific surface crosslinking liquids makes it possible to more effectively achieve excellent particle strength, liquid permeability and absorption performance required for one embodiment.

With regard to the method of adding the surface crosslinking liquid containing the surface crosslinking liquid to the base polymer powder, there is no particular limitation in the constitution. For example, a method of adding and mixing the surface crosslinking liquid and the base polymer powder in a reactor, a method of spraying the surface crosslinking liquid onto the base polymer powder, or a method of continuously feeding the base polymer powder and the surface crosslinking liquid to a mixer which is continuously operated, or the like, may be used.

The surface crosslinking liquid may further include water and/or methanol as a medium. Thus, there is an advantage that the surface crosslinking agent and the silica particles can be evenly dispersed on the base polymer powder. In this case, the content of water and methanol can be applied by adjusting the addition ratio with respect to 100 parts by weight of the base polymer powder, for the purpose of inducing the uniform dispersion of the surface crosslinking agent and the hydrophilic silica particles, preventing the phenomenon of aggregation of the base polymer powder and at the same time optimizing the surface penetration depth of the surface crosslinking agent.

The surface crosslinking reaction can be performed by heating the surface crosslinking liquid-added base polymer powder at a maximum reaction temperature of 140° C. to 200° C., or 150° C. to 190° C. for 5 minutes to 60 minutes, or 10 minutes to 50 minutes, or 20 minutes to 45 minutes. More specifically, the surface crosslinking step can be performed by subjecting to a heat treatment under the conditions in which the temperature is raised from an initial temperature of 20° C. to 130° C., or 40° C. to 120° C. to the maximum reaction temperature over a period of 10 minutes to 30 minutes, and the maximum temperature is maintained for 5 minutes to 60 minutes.

By satisfying the conditions of such a surface crosslinking step (in particular, the temperature-raising conditions and the reaction conditions at the maximum temperature of the reaction), the super absorbent polymer suitably satisfying physical properties of one embodiment can be prepared.

A means for raising the temperature for surface crosslinking reaction is not particularly limited. Heating may be performed by providing a heating medium or by directly providing a heat source. In this case, the type of the heating medium applicable herein may be a hot fluid such as steam, hot air, hot oil, or the like, but the present invention is not limited thereto. Further, the temperature of the heating medium provided may be properly controlled, considering the means of the heating medium, the temperature-raising rate, and the temperature-raising target temperature. Meanwhile, as the heat source provided directly, an electric heater or a gas heater may be used, but the present invention is not limited to these examples.

As described above, the super absorbent polymer obtained according to the above-described method maintains excellent absorption performance such as water retention capacity and absorbency under pressure and can satisfy more improved particle strength, horizontal gel strength, liquid permeability and/or absorption rate, thereby satisfying various physical properties. Accordingly, it can be suitably used for sanitary materials such as diapers, particularly, ultra-thin sanitary materials having reduced pulp content.

Advantageous Effects

According to the present invention, the super absorbent polymer maintaining excellent absorption performance such as a centrifuge retention capacity and/or an absorbency under pressure and satisfying more improved liquid permeability and/or absorption rate, and the like can be provided.

This super absorbent polymer can be suitably used for sanitary materials such as disposable diapers, particularly ultra-thin sanitary materials with reduced content of pulp.

BRIEF DESCRIPTION OF THE DRAWINGS

FIG. 1 is a photograph showing examples of surface cross-linked particles in the measurement of the surface crosslinking ratio of the super absorbent polymer of Examples and Comparative Examples.

FIG. 2 is a photograph showing an example of surface non-cross-linked particles in the measurement of surface cross-linking ratios of the super absorbent polymer of Examples and Comparative Examples.

FIG. 3 is a photograph showing an example of a large particle in which several particles are aggregated without surface crosslinking in the measurement of the surface crosslinking ratio of the super absorbent polymer of Examples and Comparative Examples.

DETAILED DESCRIPTION OF THE EMBODIMENTS

Hereinafter, the preferred Examples are provided for better understanding of the invention. However, these Examples are given for illustrative purposes only and not intended to limit the scope of the present invention.

In Examples and Comparative Examples, the contact angles of a surface crosslinking liquid and physical properties of the respective super absorbent polymers were measured and evaluated by the following methods.

(1) Contact Angle of Surface Crosslinking Liquid

After forming the surface crosslinking solution used in Examples and Comparative Examples, the contact angle was measured and evaluated by dropping on a PET substrate (Mitsuibishi Polyester Film, Grade name: O0300E).

(2) Evaluation of Particle Size

The particle sizes of the base polymer powders and the super absorbent polymers used in Examples and Comparative Examples were measured in accordance with EDANA (European Disposables and Nonwovens Association) recommended test method No. WSP 220.3.

(3) Centrifuge Retention Capacity(CRC)

For the absorbent polymers prepared in Examples and Comparative Examples, the centrifuge retention capacity (CRC) by absorption magnification under a non-loading condition was measured in accordance with EDANA (European Disposables and Nonwovens Association) recommended test method No. WSP 241.3.

That is, after uniformly inserting $W_0(g)$ (about 0.2 g) of each polymer obtained in Examples and Comparative Examples in a nonwoven fabric-made bag and sealing the same, it was soaked in a physiological saline solution composed of 0.9 wt % sodium chloride aqueous solution at room temperature. After 30 minutes, water was removed from the bag by centrifugation at 250 G for 3 minutes, and the weight $W_2(g)$ of the bag was then measured. Further, the same procedure was carried out without using the polymer, and then the resultant weight $W_1(g)$ was measured.

Using the respective weights thus obtained, the CRC(g/g) was determined according to the following Calculation Equation 1.

$$CRC(g/g) = \{[W_2(g) - W_1(g) - W_0(g)]/W_0(g)\} \quad \text{[Calculation Equation 1]}$$

in Calculation Equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is a weight of the device including the super absorbent polymer, measured after soaking the super absorbent polymer in a physiological saline solution at room temperature for 30 minutes, and then dehydrating the same by using a centrifuge at 250 G for 3 minutes.

(4) Absorbency Under Pressure (AUP)

For the absorbent polymers prepared in Examples and Comparative Examples, the absorbency under pressure was measured in accordance with EDANA (European Disposables and Nonwovens Association) recommended test method No. WSP 242.3.

First, a 400 mesh stainless steel net was installed in the cylindrical bottom of a plastic having an internal diameter of 60 mm. $W_0$(g, 0.90 g) of the absorbent polymers prepared in Examples 1-6 and Comparative Examples 1-3 were uniformly scattered on the steel net under conditions of temperature of 23±2° C. and relative humidity of 45%, and a piston which can provide a load of 4.83 kPa (0.7 psi) uniformly was put thereon. The external diameter of the piston was slightly smaller than 60 mm, there was no gap between the cylindrical internal wall and the piston, and the jig-jog of the cylinder was not interrupted. At this time, the weight $W_3$(g) of the device was measured.

After putting a glass filter having a diameter of 125 mm and a thickness of 5 mm in a Petri dish having a diameter of 150 mm, a physiological saline solution composed of 0.90 wt % of sodium chloride was poured in the dish until the surface level became equal to the upper surface of the glass filter. A sheet of filter paper having a diameter of 120 mm was put thereon. The measuring device was put on the filter paper and the solution was absorbed under a load for 1 hour. After 1 hour, the weight $W_4$(g) was measured after lifting the measuring device up.

Using the respective weights thus obtained, AUP(g/g) was calculated according to the following Calculation Equation 2, thereby confirming the absorbency under pressure.

$$AUP(g/g) = [W_4(g) - W_3(g)]/W_0(g) \qquad \text{[Calculation Equation 2]}$$

in Calculation Equation 2, $W_0$(g) is an initial weight(g) of the super absorbent polymer, $W_3$(g) is the total sum of a weight of the super absorbent polymer and a weight of the device capable of providing a load to the super absorbent polymer, and $W_4$(g) is the total sum of a weight of the super absorbent polymer and a weight of the device capable of providing a load to the super absorbent polymer, after absorbing a physiological saline solution to the super absorbent polymer under a load (0.7 psi) for 1 hour.

(5) Particle Strength

Using the Texture Analyzer (model name: XT2 Plus, TA), the particle strength of the super absorbent polymers of Examples and Comparative Examples was measured as follows.

First, the super absorbent polymer samples (30 to 50 mesh) of Examples and Comparative Examples were sieved off to collect samples having a particle size of 600 to 850 μm. A single particle of the super absorbent polymer was extracted from the collected samples. After a plate module was placed on the above measuring device, the single particle was placed on the plate module. A cylinder with a diameter of 8 mm was lowered parallel to the plate module just above the single particle. While lowering the cylinder at a speed of 0.01 mm/s, it was pressurized at a constant speed. The force with which a single particle can withstand with time was measured, and the maximum force applied to the particle until crushing was measured. The maximum force during crushing thus obtained was determined several times through experiments, and the average force thereof was calculated and defined as the particle strength.

(6) Gel Strength (G')

For the absorbent polymers/base polymer powders prepared in Examples and Comparative Examples, the horizontal gel strength was measured.

First, the absorbent polymer samples (30-50 mesh) prepared in Examples and Comparative Examples were sieved off and 0.5 g of the samples were weighed. The weighed samples were sufficiently swelled in 50 g of a physiological saline solution for 1 hour. After that, the solvent not absorbed therein was removed by using an aspirator for 4 minutes, and the solvent left on the surface of the same was evenly distributed and wiped once with a filter paper.

2.5 g of the swelled super absorbent polymer was loaded between two parallel plates (parallel plates with a 25 mm diameter, a lower plate thereof having a wall with a 2 mm height for preventing the sample from leaking) of the rheometer, and the gap (1 mm) between the parallel plates was adjusted. At this time, the gap between the parallel plates was properly adjusted by pressing the plates with a force of about 3 N so that the swelled sample was contacted evenly at the face of the plates.

A linear viscoelastic regime section of strain where the storage modulus and the loss modulus were steady was found by using the rheometer while increasing the shear strain at a 10 rad/s oscillation frequency. Generally, in the case of a swelled super absorbent polymer, a strain of 0.1% is imparted in the liner viscoelastic regime section.

The storage modulus and the loss modulus of the swelled super absorbent polymer was measured by using the strain value of the linear viscoelastic regime section at an oscillation frequency of 10 rad/s for 60 seconds. The horizontal gel strength was obtained by taking an average of the obtained storage modulus. For reference, the loss modulus was measured as a very small value as compared to the storage modulus.

(7) Saline Flow Conductivity (SFC)

The saline flow conductivity was measured in accordance with the method disclosed in Columns 54 to 59 of U.S. Pat. No. 5,562,646.

(8) Free Swell Rate (FSR)

The FSR of the base polymer powder or the super absorbent polymer was measured and calculated according to the method disclosed on pages 22 to 23 of European Patent Publication No. 2535027 using those classified into #30 to #50 (for example, those having a particle size of 300 to 600 μm).

(9) T-20

9 g of sodium chloride and 1 g of Lorodac (main component: alcohol ethoxylate having 12 to 14 linear carbon atoms, CAS #68439-50-9) were dissolved in 1 L of distilled water, and the T-20 was calculated and measured with the time required for absorbing 1 g of the super absorbent polymer to 20 g of this aqueous solution. Specific measurement method of T-20 is described in detail on pages 13 to 18 of European Patent Publication No. 2535027.

(10) Surface Crosslinking Ratio 0.5 g of a super absorbent polymer (powder having a particle size of 300 to 600 μm was classified and taken) was swollen in a physiological saline solution (0.9 wt % sodium chloride aqueous solution) to which 20 ppmw of Toluidine Blue O (TBO, CAS #92-31-9) had been added for 16 hours. After swelling, the solution and the super absorbent polymer powder were poured into a Petri dish, and then the super absorbent polymer powder was observed with a Stereotype Microscope, and the surface crosslinking ratio of the super absorbent polymer was evaluated as follows.

First, the photographs (image resolution: 1024×768, transmission mode, stereotype) of the whole particles of the super absorbent polymer after swelling at 10 magnification are photographed, and the size and length of the photographs were adjusted so that the total number of particles in the photographs was 200 to 300. Next, the paper size was set to A4 size with Microsoft's Power Point 2010 version, the photographed picture was pasted, and the picture size was adjusted to 19 cm×25.33 cm. Then, the contrast of the photograph was adjusted to about 40% in black and white, and the brightness of the photograph was adjusted at an appropriate brightness, for example, at a reflectance of about 18%.

As a result, for example, photographs as shown in FIGS. 1 to 3 were obtained. In the photographs of the images containing such whole particles, particles having stripes with a width of 2 mm or more and a length of 5 mm or more formed on the particles were observed. For reference, the stripes having a width of 2 mm or more and a length of 5 mm or more are observed while the SHELL of the super absorbent polymer of the surface cross-linked layer was broken. The degree of surface crosslinking could be confirmed and evaluated by the traces that the SHELL was broken by swelling.

As shown in FIG. 1, particles having stripes with a width of 2 mm or more and a length of 5 mm or more formed on the particles were evaluated as surface cross-linked super absorbent particles, and as shown in FIGS. 2 and 3, particles without stripe formation can be evaluated as surface non-cross-linked particles. For reference, FIG. 2 is a photograph showing an example of surface non-cross-linked super absorbent polymer particles in which stripe patterns were not formed on the single particle. FIG. 3 is a photograph showing an example of a large particle in which several particles were aggregated. The stripe patterns were not observed also on such a large particle, and it was evaluated that it was not surface-cross-linked.

Under this criterion, the ratio of numbers of the surface cross-linked particles among the particles of the entire super absorbent polymer produced under the same conditions was calculated by the surface cross-linkage ratio. The surface cross-linking ratio was calculated according to the following formula: Surface crosslinking ratio (%)=["Number of particles evaluated as surface cross-linked particles"/"Number of total particles in photograph"]×100.

Example 1

100 g of acrylic acid, 0.5 g of polyethylene glycol diacrylate (Mw=523) as a crosslinking agent, 83.3 g of 50% caustic soda (NaOH), and 89.8 g of water were mixed to prepare a monomer aqueous solution composition having a monomer concentration of 45% by weight.

Subsequently, 810 g of the monomer aqueous solution was first mixed with 30.54 g of a 0.18% ascorbic acid solution and 33 g of a 1% sodium persulfate solution, and the mixture was fed through a feed section of a continuous polymerization reactor with a kneader, together with 30.45 g of a 0.15% hydrogen peroxide solution, so as to perform polymerization. At this time, temperature of the polymerization reactor was maintained at 80° C., and the maximum polymerization temperature was 110° C. and the polymerization time was 1 min and 15 s. Thereafter, kneading was continuously performed, and polymerization and kneading were performed for 20 min. Thereafter, the size of the polymer produced was distributed to less than 0.2 cm. At this time, the water content of the hydrogel polymer finally formed was 51% by weight.

Subsequently, the gel pulverization was performed by using Meat Chopper (SL Company, SM3-2) pulverizing device, and using a gel-pulverizing device in which an inverter for axis control (for example, manufacturer: LS Industrial Systems, model name: iG5A) was installed, an S-13 mm perforated plate (for example, an aperture ratio of 25%) having a diameter of 10 mm was installed. More specifically, the gel pulverization was performed by rotating the shaft at a speed of 60 Hz while passing the hydrogel polymer through a pulverizing device.

Subsequently, the resulting polymer was dried in a hot-air dryer at a temperature of 175° C. for 30 minutes, and the dried hydrogel polymer was pulverized by the following method.

First, as the pulverizing device, a food mixer type pulverizing device (manufacturer: HANIL, model name: HMF-30005) was used, 500 g of the dried polymer powder was placed in the pulverizing device, and pulverized for 15 seconds with strength "weak", and additionally 500 g was further used and pulverized by the same method.

1 kg of the polymer powder thus pulverized was put in a classifier (Restsch, AS200) and classified with an amplitude of 1.5 mm into five mesh sizes (combination of classified meshes: #25/#30/#50/#100/PAN), and respective classified particles were collected. Then, the large particles collected on the #25 sieve were additionally pulverized for 15 seconds, and such additional pulverization was two times.

Through the above-described method, a polymer having a particle size of about 150 μm to 850 μm was classified and obtained. After the base polymer powder was obtained by the above method, the FSR thereof was measured. As a result, it was confirmed to be 0.24 g/g·s.

Thereafter, based on 100 parts by weight of the base resin powder, 0.4 part by weight of ethylene carbonate, 3.5 parts by weight of water, 0.04 part by weight of fumed silica particles (Aerosil 200), 0.01 part by weight of colloidal silica particles (ST-O), and 0.05 part by weight of the polycarboxylic acid-based copolymer disclosed in Preparation Example 1 of Korean Patent Laid-open Publication No. 2015-0143167 (Korean Patent Application No. 2014-0072343) were mixed to form a surface treatment solution. Such a surface treatment solution was sprayed onto the base polymer powder, stirred at room temperature, and mixed so that the surface treatment liquid was evenly distributed on the base polymer powder.

Thereafter, the base polymer powder was placed in a surface crosslinking reactor and the surface cross-linking reaction was performed.

In the surface crosslinking reactor, it was confirmed that the base polymer powder was gradually heated at an initial temperature near 20° C. After 20 minutes elapsed, operation was performed so as to reach the maximum reaction temperature of 185° C. After reaching the maximum reaction temperature, additional reaction was carried out for 40 minutes, and a sample of the finally produced super absorbent polymer was taken. After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 2

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 0.04 part by weight of fumed silica particles (Aerosil 200), 0.02 part by weight of colloidal silica particles (ST-O), and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 3

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 0.04 part by weight of fumed silica particles (Aerosil 200), 0.03 part by weight of colloidal silica particles (ST-O), and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 4

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 0.04 part by weight of fumed silica particles (Aerosil 200), 0.04 part by weight of colloidal silica particles (ST-O), and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 5

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 0.02 part by weight of fumed silica particles (Aerosil 200), 0.06 part by weight of colloidal silica particles (ST-O), and 0.05 part by weight of the same polycarboxylic acid-based copolymer as disclosed in Example 1 were mixed to form a surface treatment solution. Subsequently, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 6

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 3.5 parts by weight of methanol, 0.02 part by weight of fumed silica particles (Aerosil 200), 0.06 part by weight of colloidal silica particles (ST-O), and 0.05 part by weight of the same polycarboxylic acid-based copolymer as disclosed in Example 1 were mixed to form a surface treatment solution. Subsequently, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 7

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 3.5 parts by weight of methanol, 0.04 part by weight of fumed silica particles (DM30S), 0.06 part by weight of colloidal silica particles (ST-O), and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 8

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 3.5 parts by weight of methanol, 0.04 part by weight of fumed silica particles (Aerosil 200), 0.06 part by weight of colloidal silica particles (ST-AK), and 0.05 part by weight of the same polycarboxylic acid-based copolymer as disclosed in Example 1 were mixed to form a surface treatment solution. Subsequently, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Example 9

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, 3.5 parts by weight of methanol, 0.04 part by weight of fumed silica particles (DM30S), 0.06 part by weight of colloidal silica particles (ST-AK), and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Comparative Example 1

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of ethylene carbonate, 3.5 parts by weight of water, and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Comparative Example 2

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of 1,3-propanediol, 0.05 part by weight of the same polycarboxylic acid-based copolymer as disclosed in Example 1 and 3.5 parts by weight of water were mixed to form a surface treatment solution. Then, surface crosslinking was carried out in the same manner as in Example 1. After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

Comparative Example 3

A base polymer powder was prepared in the same manner as in Example 1. The FSR thereof was measured, and as a result, it was confirmed to be 0.24 g/g·s.

Thereafter, based on 100 parts by weight of the base resin powder, 0.4 part by weight of 1,3-propanediol, 3.5 parts by weight of water, 0.5 part by weight of aluminum sulfate and 0.05 part by weight of the same polycarboxylic acid-based copolymer as disclosed in Example 1 were mixed to form a surface treatment solution. Then, surface crosslinking was carried out in the same manner as in Example 1.

After the surface crosslinking step, a surface cross-linked super absorbent polymer having a particle size of about 150 to 850 μm was obtained by using a sieve. The content of the fine powder having a particle size of about 150 μm or less in the product of the super absorbent polymer was less than 1.0 wt %.

For the super absorbent polymers of Examples 1 to 9 and Comparative Examples 1 to 3, the physical property measurement and evaluation of CRC, AUP, SFC, gel strength (G'), T-20 and surface crosslinking ratio were carried out, and the measured physical property values are shown in Table 1 below.

TABLE 1

|  | Surfaces crosslinking ratio(%) | CRC (g/g) | AUP (g/g) | SFC ($\cdot 10^{-7}$ cm$^3 \cdot$ s/g) | T-20(s) | Particel strength (kgf) | Gel strength (Pa) |
| --- | --- | --- | --- | --- | --- | --- | --- |
| Example 1 | 35.7 | 27.2 | 24.1 | 69 | 173 | 1.61 | 11405 |
| Example 2 | 40.8 | 27.4 | 23.5 | 84 | 152 | 1.73 | 11047 |
| Example 3 | 43.1 | 27.3 | 23.8 | 94 | 138 | 1.82 | 11153 |
| Example 4 | 45.6 | 27.6 | 24.4 | 116 | 145 | 2.01 | 12553 |
| Example 5 | 46.2 | 27.1 | 24.1 | 112 | 152 | 1.91 | 12027 |
| Example 6 | 42.1 | 27.3 | 23.7 | 90 | 140 | 1.58 | 11305 |
| Example 7 | 47.3 | 27.4 | 23.8 | 98 | 152 | 1.52 | 10069 |
| Example 8 | 42.1 | 27.9 | 23.6 | 87 | 156 | 1.55 | 11203 |
| Example 9 | 46.2 | 27.3 | 23.5 | 91 | 145 | 1.53 | 11032 |
| Comparative Example 1 | 26.0 | 26.2 | 21.6 | 47 | 160 | 1.23 | 9006 |
| Comparative Example 2 | 22.1 | 26.4 | 21.1 | 43 | 156 | 1.17 | 9001 |
| Comparative Example 3 | 26.3 | 25.8 | 21.8 | 48 | 133 | 1.10 | 9332 |

Referring to Table 1, it was confirmed that Examples exhibited not only high surface crosslinking ratio, excellent absorption performance (particularly, absorbency under pressure) and liquid permeability, but also excellent particle strength and gel strength and the like as compared with Comparative Examples. Particularly, it was confirmed that Examples exhibited excellent physical properties by using various colloidal silica particles and fumed silica particles during surface crosslinking.

The invention claimed is:

1. A super absorbent polymer comprising:
   a base polymer powder including a first cross-linked polymer of a water-soluble ethylenically unsaturated monomer having at least partially neutralized acidic groups; and
   a surface cross-linked layer formed on the base polymer powder and including a second cross-linked polymer in which the first cross-linked polymer is further cross-linked via an alkylene carbonate having 2 to 5 carbon atoms,
   wherein the super absorbent polymer has the following features:
   a centrifuge retention capacity (CRC) for a physiological saline solution (0.9 wt % sodium chloride aqueous solution) for 30 minutes is 25 to 35 g/g,
   an absorbency under pressure (AUP) under 0.7 psi for a physiological saline solution (0.9 wt % sodium chloride aqueous solution) for 1 hour is 23.5 to 30 g/g,
   a saline flow conductivity (SFC) for a physiological saline solution (0.685 wt % sodium chloride aqueous solution) ($10^{-7}$ cm$^3$·s/g) is 60 to 130 ($10^{-7}$ cm$^3$·s/g),
   a particle strength is 1.5 kgf to 2.5 kgf, and
   a horizontal gel strength (G'), measured after absorbing and swelling a physiological saline solution for 1 hour, is 10,000 to 15,000 Pa, wherein the physiological saline solution is 0.9 wt % sodium chloride aqueous solution.

2. A super absorbent polymer comprising:
   a base polymer powder including a first cross-linked polymer of a water-soluble ethylenically unsaturated monomer having at least partially neutralized acidic groups; and
   a surface cross-linked layer formed on the base polymer powder and including a second cross-linked polymer in which the first cross-linked polymer is further cross-linked through an alkylene carbonate having 2 to 5 carbon atoms,
   wherein the super absorbent polymer has the features:
   a centrifuge retention capacity (CRC) for a physiological saline solution (0.9 wt % sodium chloride aqueous solution) for 30 minutes is 25 to 35 g/g,
   an absorbency under pressure (AUP) under 0.7 psi for a physiological saline solution (0.9 wt % sodium chloride aqueous solution) for 1 hour is 23.5 to 30 g/g,
   a saline flow conductivity (SFC) for a physiological saline solution (0.685 wt % sodium chloride aqueous solution) ($10^{-7}$ cm$^3$·s/g) is 60 to 130 ($10^{-7}$ cm$^3$·s/g),
   T-20 indicating the time required for absorbing 1 g of the super absorbent polymer to 20 g of an aqueous solution of sodium chloride and alcohol ethoxylate having 12 to 14 carbon atoms, is 100 to 190 seconds, and
   a particle strength is 1.5 kgf or more, and
   a horizontal gel strength (G'), measured after absorbing and swelling a physiological saline solution for 1 hour, is 10,000 to 15,000 Pa, wherein the physiological saline solution is 0.9 wt % sodium chloride aqueous solution.

3. The super absorbent polymer of claim 1 or 2, further comprising fumed silica particles and colloidal silica particles dispersed on the surface cross-linked layer.

4. The super absorbent polymer of claim 1 or 2, wherein the super absorbent polymer has a crosslinking ratio of 30% to 90%, wherein the crosslinking ratio is measured after swelling the super absorbent polymer in a physiological saline solution (0.9 wt % sodium chloride aqueous solution) to which 20 ppmw of Toluidine Blue 0 (TBO, CAS #92-31-9) has been added for 16 hours is 30% to 90%.

5. The super absorbent polymer of claim 1 or 2, wherein the first cross-linked polymer is formed by subjecting a monomer to a crosslinking polymerization in the presence of at least one internal crosslinking agent selected form the group consisting of bis(meth)acrylamide having 8 to 12 carbon atoms, poly(meth)acrylate of polyol having 2 to 10 carbon atoms and poly(meth)acrylate having 2 to 10 carbon atoms.

6. The super absorbent polymer of claim 1 or 2, wherein it has a particle size of 150 to 850 μm.

7. The super absorbent polymer of claim 1 or 2, wherein the water-soluble ethylenically unsaturated monomer includes at least one selected from the group consisting of anionic monomers, non-ionic, hydrophilic group-containing monomers, and amino group-containing unsaturated monomers.

8. The super absorbent polymer of claim 7, wherein the anionic monomers are selected from the group consisting of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid, 2-(meth)acrylamido-2-methylpropanesulfonic acid, and salts thereof.

9. The super absorbent polymer of claim 7, wherein the non-ionic, hydrophilic group-containing monomers are selected from the group consisting of (meth)acrylamide, N-substituted (meth)acrylate, 2-hydroxyethyl(meth)acrylate, 2-hydroxypropyl(meth)acrylate, methoxypolyethylene glycol(meth)acrylate, and polyethylene glycol (meth)acrylate.

10. The super absorbent polymer of claim 7, wherein the amino group-containing unsaturated monomers are selected from the group consisting of (N,N)-dimethylaminoethyl (meth)acrylate, (N,N)-dimethylaminopropyl(meth)acrylamide, and quaternary products thereof.

* * * * *